(12) United States Patent
Whitmore, III et al.

(10) Patent No.: US 9,220,575 B2
(45) Date of Patent: Dec. 29, 2015

(54) ACTIVE MARKER DEVICE FOR USE IN ELECTROMAGNETIC TRACKING SYSTEM

(75) Inventors: Willet F. Whitmore, III, Longboat Key, FL (US); Roger F. Wilson, Sarasota, FL (US)

(73) Assignee: Civco Medical Instruments Co., Inc., Kalona, IA (US)

( * ) Notice: Subject to any disclaimer, the term of this patent is extended or adjusted under 35 U.S.C. 154(b) by 1035 days.

(21) Appl. No.: 12/984,901

(22) Filed: Jan. 5, 2011

(65) Prior Publication Data

US 2011/0166446 A1 Jul. 7, 2011

Related U.S. Application Data

(60) Provisional application No. 61/292,586, filed on Jan. 6, 2010.

(51) Int. Cl.
*A61B 5/05* (2006.01)
*A61B 19/00* (2006.01)
*A61B 17/00* (2006.01)

(52) U.S. Cl.
CPC ....... *A61B 19/54* (2013.01); *A61B 2017/00951* (2013.01); *A61B 2019/5251* (2013.01); *A61B 2019/5483* (2013.01); *A61B 2019/5495* (2013.01)

(58) Field of Classification Search
USPC .................................................. 604/103, 529
See application file for complete search history.

(56) References Cited

U.S. PATENT DOCUMENTS

| | | | |
|---|---|---|---|
| 6,119,033 A | 9/2000 | Spigelman et al. | |
| 6,381,485 B1 | 4/2002 | Hunter et al. | |
| 2006/0229641 A1* | 10/2006 | Gupta et al. | 606/130 |
| 2007/0106305 A1* | 5/2007 | Kao et al. | 606/130 |
| 2007/0208352 A1* | 9/2007 | Henderson et al. | 606/130 |
| 2009/0213997 A1 | 8/2009 | Maschke | |

FOREIGN PATENT DOCUMENTS

| | | |
|---|---|---|
| WO | 9835720 | 8/1998 |
| WO | 9838919 | 9/1998 |
| WO | 9905973 | 2/1999 |
| WO | 2004075768 A2 | 9/2004 |
| WO | 2008142629 A2 | 11/2008 |

OTHER PUBLICATIONS

International Search Report re Application No. PCT/US2011/020265 dated Apr. 28, 2011.

* cited by examiner

*Primary Examiner* — Unsu Jung
*Assistant Examiner* — Shahdeep Mohammed
(74) *Attorney, Agent, or Firm* — Caesar Rivise, PC

(57) ABSTRACT

A device for use in an image-guided procedure on a patient is disclosed. The device includes an EM sensor assembly, a frame assembly (e.g., a base portion from which a plurality of legs project upward to a common point) and a plurality of attachment members. Each attachment member is arranged to be releasably (e.g., adhesively) secured to the skin of a patient and to be coupled to the frame assembly to secure the frame assembly on the skin of the patient. The EM sensor assembly is arranged to be releasably secured to the frame assembly (e.g., pivotably snap-fit into a socket in the frame assembly). The device additionally includes plural visualizable elements (e.g., metal balls) that are adapted to be readily imaged to establish imaging reference points and a plurality of asymmetrically disposed apertures to enable tattooing indicia on the skin of the patient through the apertures.

11 Claims, 5 Drawing Sheets

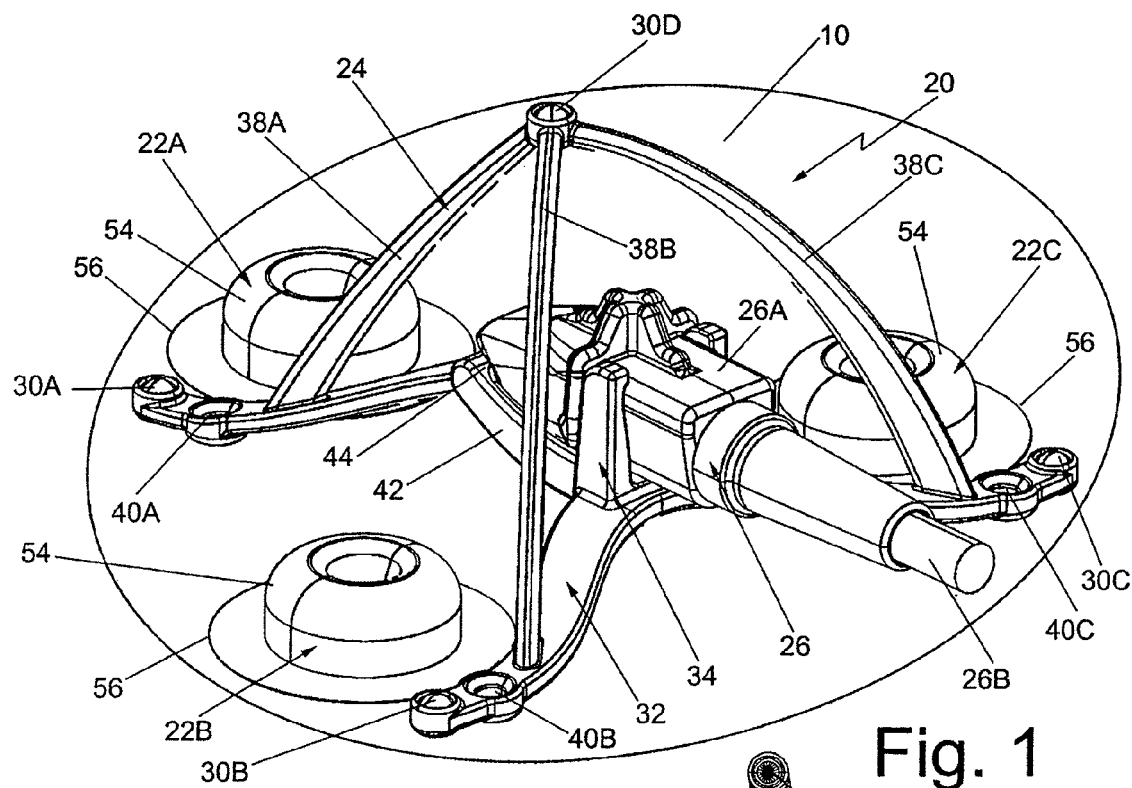

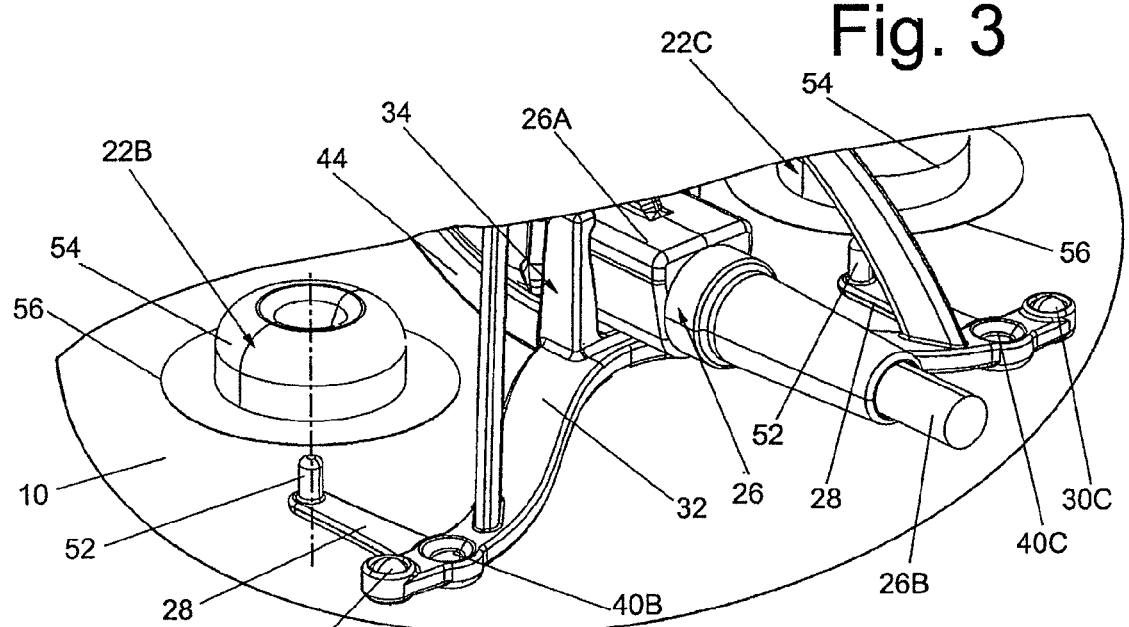
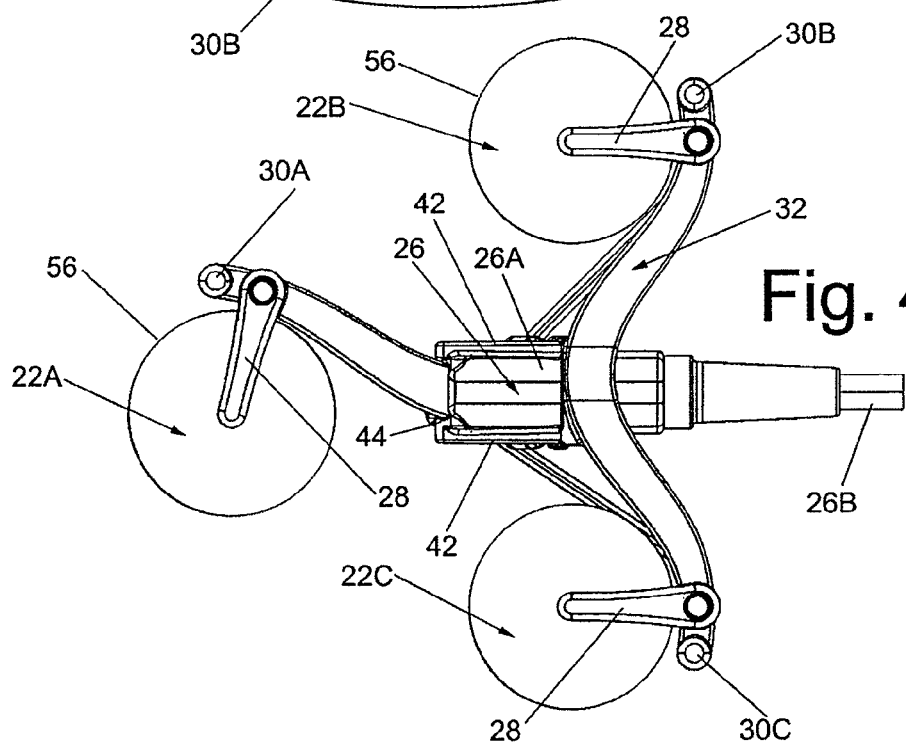

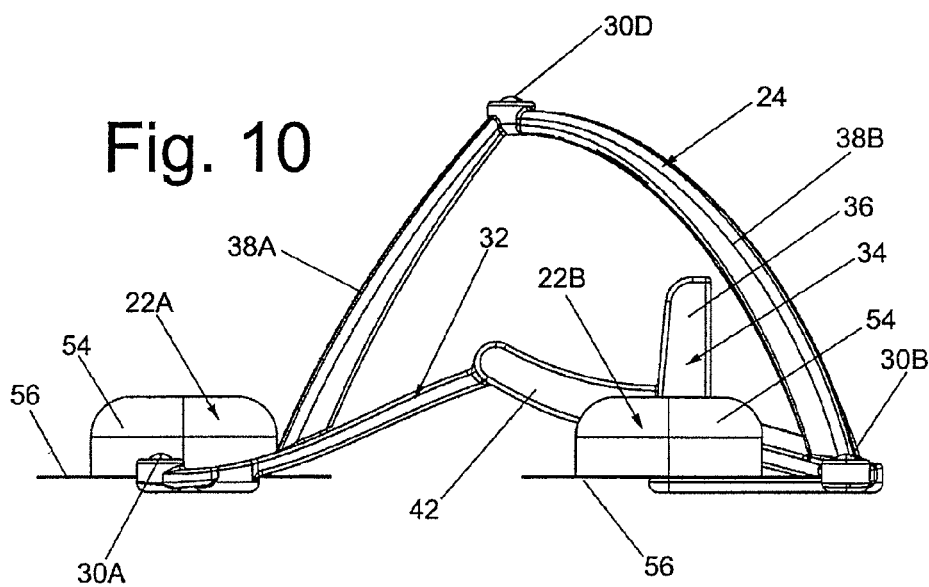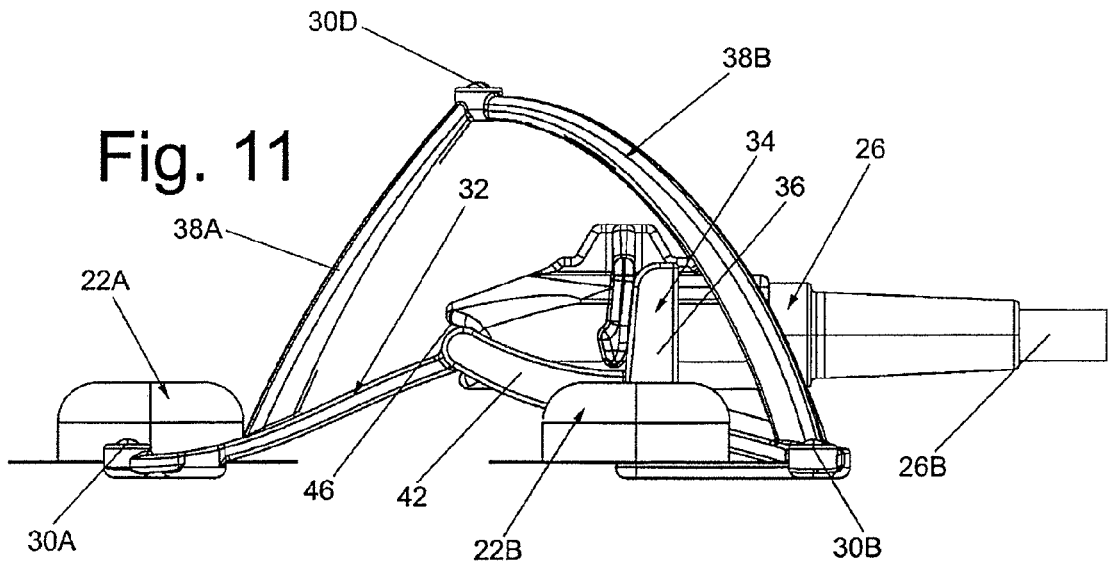

ACTIVE MARKER DEVICE FOR USE IN ELECTROMAGNETIC TRACKING SYSTEM

CROSS-REFERENCE TO RELATED APPLICATIONS

This utility application claims the benefit under 35 U.S.C. §119(e) of Provisional Application Ser. No. 61/292,586 filed on Jan. 6, 2010 and entitled Active Marker for Use in Electromagnetic Tracking System, the entire disclosure of which is incorporated by reference herein.

FIELD OF THE INVENTION

This invention relates generally to medical instrument tracking systems and more particularly active marker devices for use in electromagnetic (EM) field multidimensional tracking systems involving the use of medical images (both 2-D and 3-D data sets of real time and/or delayed and/or fused images) to register to a patient.

BACKGROUND OF THE INVENTION

As is known, optical and electromagnetic tracking (EMT) technologies are two non-mechanical, real-time, approaches for accurate medical instrument tracking and navigation using appropriately registered volume images (digital data sets). Both optical and electromagnetic technologies have advantages and limitations, but on balance the technological advantages of EMT for minimally invasive procedures are dominant. In particular, EMT is believed to be the preferable technology because of the ability to track objects inside the body (beyond line-of sight) and the compact size of the tracked sensors. These powered sensors typically provide position and orientation data sets of 5 or 6 degrees-of-freedom (DOF) and combined with the electronic cables required are relatively expensive.

EMT systems that support image fusion and instrument tracking are commercially available and some are disclosed in the patent literature. They typically enable determination of 5 or 6 DOF orientation and position of an instrument, such as a needle, by determining location, orientation, and/or positioning information relative to some coordinate system. For example, Ascension Technology Corporation makes 5 and 6 DOF position and orientation tracking devices suitable for various medical applications, e.g., to navigate, localize, and guide medical instruments for image-guided procedures. Other manufacturers/suppliers of EM tracking systems include Polhemus, Inc., Northern Digital Inc. and Medtronic, Inc. Suppliers of software, tracked needles and other instruments for clinical use that utilize these technologies in medical procedures include Traxtal Corporation, Veran Medical and Medtronic, Inc. Image fusion in combination with ultrasound is available from Traxtal, Inc., GE Healthcare Ultrasound and Esaote Ultrasound, among others.

Typically these tracking systems use the attenuation of oriented electromagnetic signals to determine the absolute position and orientation of a sensor, relative to a source, e.g., a magnetic field generator. The source and the sensor typically are connected via cables to an electronics module, which contains a microcomputer and associated electronics of the system. The source typically includes three orthogonal coils that are pulsed in rotation, one after another. Each pulse transmits a radio frequency electromagnetic signal that is detected by the sensor. The sensor also contains two or three orthogonal coils, which measure the strength of the signal from the current source coil. By using the known pulse strength at the source and the known attenuation of the strength with distance, the position and orientation of the sensor coils can be calculated by the system via triangulation techniques.

External markers are commonly used to identify surface (skin) locations on a patient during image-guided medical procedures. These markers typically attach with adhesive and are seen as a point, a series of points, or a grid by the imaging technology being used. Some markers are "seen" by only a single imaging modality (e.g., x-ray), while others may be well seen in multiple modalities (e.g., CT (x-ray) and MR). Surface markers of this type can also be used to assist with 3-D image fusion, where a 3-D image data set is acquired in one modality (e.g. CT) and then fused with a 3-D data set from another taken earlier (e.g., MR), or fused in real time with 2-D data sets, such as ultrasound, to facilitate the targeting of lesions within the body. In these cases the markers may be used as points of reference to help align or register the image data sets. Accurate registration is critical to achieving useful image fusion, and the greater the number of common points that are in a known position on both data sets, and the more accurate these known positions, the greater the accuracy and usefulness of the fused images. Attaching 5 or 6DOF electromagnetic sensors to surface markers in a known orientation permits registration of a 3-D imaging data set that includes these markers with the electromagnetic field of an electromagnetic navigation system. Specifically, one 6DOF sensor associated with at least 4 markers that are not coplanar, or two 5DOF sensors that are associated with at least two markers each that are oriented so as to avoid being co-planar can provide 3-D registration. Such markers are being used in currently available electromagnetic navigation medical systems. However, two problems are not addressed by these devices. One is the expense created by having the relatively expensive electromagnetic sensors and cables permanently embedded in these component markers that must be disposed of after a single use to avoid patient-to-patient contamination. The second is the inability to place, remove and then replace the marker in the same location on a patient at a different time. This can be critical to the marker's use for registration because the best images for visualizing a tumor or other internal lesion, in many cases, may be obtained at an initial diagnostic or treatment planning imaging procedure (e.g., CT, PET-CT or MR scan) that is not concurrent with the therapeutic procedure.

A need exists for a marker device, which allows inclusion of an EM sensor, which also can be readily and reproducibly secured to the body of a patient for use, and which may be disposable, but will enable the reuse of the sensor, since that component is relatively expensive.

The subject invention addresses that need by providing an active marker device that includes disposable (e.g., one-time use) components that is releasably and reproducibly secureable to the skin of the patient while permitting re-use of the much more expensive sensor assembly. Since the sensor assembly is a significantly expensive component of an EMT system, the subject invention enables users to greatly reduce costs per procedure in the rapidly expanding market for image fusion and guidance. While re-using the expensive 5 or 6 DOF powered (active) EM sensors will require a more complex setup and assembly process for each use, the payoff in reduced cost per procedure is believed to be so critical that the small extra time required for such set-up will likely be gladly tolerated.

Moreover, the subject invention is designed with a universal approach allowing it to be used across all OEM imaging platforms. In particular, it is anticipated that the subject invention will be utilized by physicians in the following specialties: interventional radiology, radiology, surgery and cardiology. Anticipated clinical applications are biopsy procedures, ablation procedures, catheter placements, intravascular procedures and endoscopic procedures.

The present invention basically comprises a device that is easily attached to the skin and easily removed via plural releasably securable attachment members, e.g., adhesive disks, each creating a respective attachment point. These attachment points are oriented like a tripod with sufficient spacing to produce a stable position and orientation on the patient's skin surface. Moreover, the device also includes a frame assembly which contains four visualizable elements establishing four respective reference points that are readily seen in CT and/or MR imaging and which do not interfere with the images. The four reference points are unequally spaced and are not coplanar, the combination of which facilitates software identification and orientation within any 3-D image set that includes the four points. The frame assembly also includes a receptacle or socket for releasably receiving a 6DOF electromagnetic sensor. That sensor is contained in a shaped housing and when releasably mounted in the socket is in a single, reproducible orientation. The socket itself is in a fixed and known orientation to the four reference points. The sensor's electrical components are located in a calibrated location within the sensor's housing. Thus, the 6DOF sensor has a known, fixed relationship to the four reference points and can be inserted to a stable position and removed as required.

Also, the frame assembly of the marker device, in addition to having a "tripod" set of legs that support it and the adhesive attachments, has three, asymmetrically spaced holes or apertures in a common plane in the base portion of the frame assembly. These apertures allow the operator to mark or "tattoo" the patient's skin with visible indicia using the singular orientation of the device's frame assembly. The marker device of this invention can then be placed at the time of an imaging exam and within the field being imaged. The skin can be marked using these three apertures as a guide for accurate future re-placement of an identical marker. Then, if the patient is in the same basic physical position at this subsequent procedure, any new images obtained in the region of the marker may be more quickly and accurately fused to the earlier image data to take advantage of any additional information that may be present. Thus, for example: if this marker was placed on the skin in the region of the liver at the time of a diagnostic CT performed with IV contrast with the patient in supine position, and a lesion was demonstrated in the liver that could only be seen with IV contrast, then, if the patient was to have a subsequent percutaneous biopsy or ablation of this lesion in the supine position, an identical marker could be re-placed on the skin in the same position and be used as a reference to register the location of this lesion in the liver on new CT images obtained at this later time without the need for additional IV contrast to illuminate it.

All references cited and/or identified herein are specifically incorporated by reference herein.

SUMMARY OF THE INVENTION

In accordance with one aspect of the invention there is provided a marker device for use in an image-guided procedure on a patient. The marker device comprises an EM sensor, a frame assembly and releasably securable attachment members, e.g., adhesive disks. Each disk is arranged to be releasably (e.g., adhesively) secured to the skin of a patient and to be coupled to the frame assembly to secure the frame assembly at a predetermined position on the body of the patient. The EM sensor is arranged to be releasably secured, e.g., pivotably snap-fit, to the frame assembly, e.g., within a socket in the frame assembly. The marker device additionally comprises plural visualizable elements, e.g., metal (or other radio-opaque and MR visualizable) balls, adapted to be readily imaged to establish plural imaging reference points.

In accordance with another aspect of this invention there is provided an attachment member, e.g., a disk, for use with a marker device in an image-guided procedure on a patient. The marker device includes an EM sensor and a frame assembly. The frame assembly includes a base portion having plural projections. The disk has an adhesive undersurface and an opening for receipt of a respective one of the plural projections of the marker device. Each disk is arranged to be releasably coupled to the frame assembly of the marker device by locating a respective one of the projections in the opening of the disk and then adhesively secured to the skin of the patient, whereupon the marker device is releasably secured to the patient.

In accordance with another aspect of this invention there is provided a frame assembly for use with an EM sensor and plural markers in an image-guided procedure on a patient. The frame assembly comprises a base portion including a socket. The socket is arranged for releasably mounting the EM sensor therein. The base portion has plural projections, each of which has an aperture or opening that is at a different distance from the others. The apertures are arranged for tattooing the skin, whereupon the frame assembly can be releasably secured to the patient at exactly the same location and orientation at different times.

DESCRIPTION OF THE DRAWING

FIG. 1 is an isometric view of one exemplary embodiment of an active marker device constructed in accordance with this invention and comprising plural (e.g., 3) releasably securable attachment members (e.g., adhesive disks), a frame assembly containing a plurality of visualizable markers and an EM sensor assembly;

FIG. 2 is a slightly reduced top plan view of just the frame assembly of the active marker device shown in FIG. 1;

FIG. 3 is a partial isometric view, somewhat similar to FIG. 1, but showing the mounting of two releasably securable attachment members on the frame assembly to secure the active marker device to the body of a patient;

FIG. 4 is a slightly reduced bottom plan view of the device of FIG. 1, but showing a complete active marker device ready to be secured to the body of a patient;

FIG. 10 is a side elevation view of the active marker device of FIG. 1 before the mounting of the sensor assembly on the frame assembly;

FIG. 11 is a side elevation view, similar to FIG. 10, but showing the device of FIG. 1 after the mounting of the sensor assembly on the frame assembly;

DETAILED DESCRIPTION OF THE PREFERRED EMBODIMENT

Figure 8:
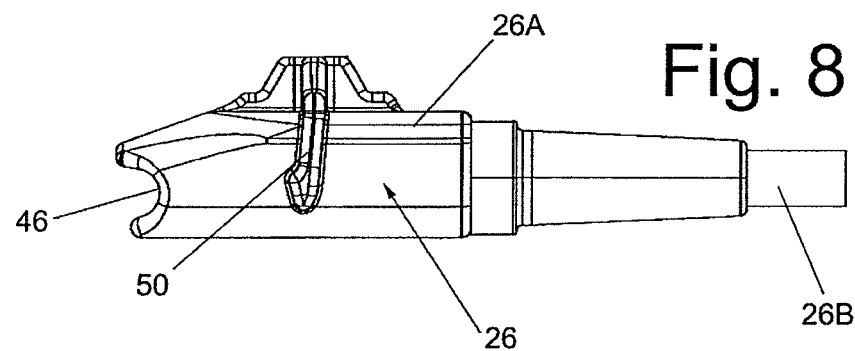
FIG. 8 is an enlarged side elevation view of the sensor assembly forming a portion of the active marker device shown in FIG. 1.
Figure 9:
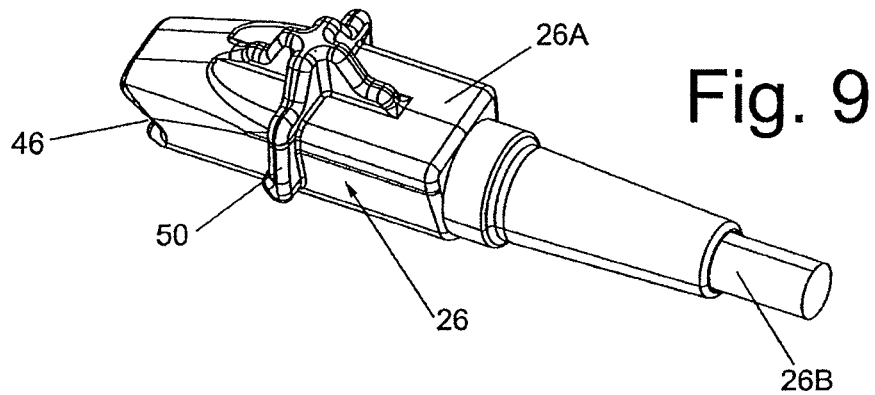
FIG. 9 is an isometric view of the sensor assembly shown in FIG. 8.

Referring now to the various figures of the drawing wherein like reference characters refer to like parts, there is shown in FIG. 1 an active marker device 20 constructed in accordance with this invention for use in an EM tracking system (not shown). The device 20 basically comprises a plurality of releasably securable attachment members, e.g., adhesive disks, 22A, 22B and 22C, a frame assembly 24 and an EM sensor assembly 26. The details of the frame assembly 24 and the sensor assembly 26 will be described later. Suffice it for now to state that in the exemplary embodiment shown the sensor assembly 26 includes a 6DOF electromagnetic sensor (not shown) contained in a particularly shaped housing 26A (FIGS. 1, 8 and 9). The frame assembly 24 includes a plurality of extension members 28 (to be described later) to which respective ones of the adhesive disks 22A, 22B and 22C may be releasably secured.

The device 20 is arranged to be releasably secured to the skin 10 of the patient via the disks 22A-22C. The disks 22A-22C can themselves serve as passive markers facilitating placement of the device 20 at the desired location on the patient. The frame assembly 24 includes a plurality of visualizable elements 30A, 30B, 30C and 30D (to be described later) which serve as reference points for the EM tracking system. The securement of the disks 22A-22C to the skin of the patient is effected by means of a releasable adhesive. Thus, the device 20 can be easily attached to the patient's skin 10 (FIG. 1) and also easily removed.

As will be appreciated from the discussion to follow later, the attachment points provided by the disks 22 and the associated portions of the frame assembly 24 are oriented like a tripod, with sufficient spacing to produce a stable position and orientation on the skin surface.

The frame assembly's elements 30A-30D will be described in detail later. Suffice it for now to state that these reference points can be readily seen in CT and/or MR imaging, but do not interfere with the images. Moreover, they are mounted so that they are unequally spaced and are not coplanar, the combination of which facilitates software identification and orientation within any 3-D image set that includes the four points.

The sensor assembly 26, itself, is arranged to be releasably mounted (secured) on the frame assembly. To that end, the frame assembly includes a base portion 32 having a socket 34 (also to be described later). The frame assembly also includes three legs 38A, 38B and 38C extending upward from the base portion 32. The legs 38A, 38B and 38C merge together at the top of the frame assembly above the socket 34 to form a tripod-like arrangement. The socket is particularly shaped for releasably receiving (mounting) the sensor assembly 26 in a single, reproducible orientation. To that end, the socket 36 is in a fixed and known orientation to the four reference points 30A-30D that can be seen on the images and includes a pair of spaced-apart upstanding arms 36.

The 6DOF EM sensor (not shown) of the sensor assembly 26 is in a calibrated location within the sensor housing 26A. Thus, the 6DOF sensor has a known, fixed relationship to the four reference points 30A-30D and can be inserted to a stable position and removed as required.

The frame assembly 24 in addition to having a "tripod" set of legs 38A, 38B and 38C that support it and the adhesive attachments provided by the adhesive disks 22A-22C, has three, asymmetrically spaced openings or apertures 40A, 40B and 40C in a common plane in the base portion 32. As best seen in FIGS. 1 and 2 the apertures 40A, 40B and 40C are located adjacent a respective one of the legs 38A, 38B and 38C. Each of the apertures is at a different distance from the others. The apertures allow the operator to mark or "tattoo" indicia on the skin of the patient using the singular orientation of the device's frame. In particular, the marker device 20 can be placed on the patient's skin at the time of an imaging exam and within the field being imaged. The skin can be marked using these three apertures as a guide at that time. Then at a later time an identical marker device 20 can be replaced in the exact same position and orientation by using the skin marks as a guide to placement. By then attaching the 6DOF sensor in its housing, the prior 3-D image data set may be immediately registered to a real time electromagnetic field and any 3-D image data set that may then be in use and registered to that field.

The details of the sensor assembly 26 will now be described. To that end, the sensor housing 26A is a small plastic member having an engineered shape that suits various purposes. The primary purpose is for releasably locking it within the socket 34 in a predetermined orientation. In particular, the socket 34 includes the heretofore identified pair of arms 36 and a pair of elongated side rails 42 (FIGS. 1 and 2). The arms 36 project upward from respective ones of the side rails 42. The front end of the socket 34, i.e., the front end of the side rails 42, is in the form of a horizontally disposed rod or pin 44. The pin 44 is arranged to be received within a correspondingly shaped recess 46 in the front end of the sensor housing 26A, as will be described later. The space between the arms 42 and the extension 44 forms a cavity for receipt of the sensor assembly 26. The upper end of each arm 42 is in the form of an inwardly projecting tab 48 (FIGS. 1-3). The pin 44 serves as a pivot point about which the sensor assembly 26 can rotate to releasably mount it to the socket (as will be described shortly).

Before doing that a brief discussion of the details of the construction of the EM sensor assembly 26 is in order. To that end, as best seen in FIGS. 8 and 9, the sensor assembly 26 basically comprises a generally parallelepiped shaped housing 26A in which the EM sensor itself (the electrical component, e.g., the EM coils) is mounted. An electrical cable 26B for the sensor exits the housing 26A at the proximal end. The corner of the housing 26A at the distal end (i.e., the end opposite from the cable egress end) includes the heretofore mentioned recess 46. The recess is of semi-circular shape and extends across the width of the housing. The radius of the recess 46 is the same or just slightly larger than the radius of the pin 44 of the socket 34. The sensor housing 26A also includes a pair of guide members 50 on opposite sides thereof. The inner end of each guide member is in the form of a sloped cam surface. The function of the guide members will be described later.

As mentioned earlier the frame assembly 24 is arranged to be releasably (e.g., adhesively) secured to the skin 10 of the patient by means of the adhesive disks 22A-22C. To that end, the base portion of the frame assembly 24 includes plural rod-like members or projections 52 projecting upward from respective ones of the extensions 28 of the frame assembly's base portion 32. Each projection 52 is disposed adjacent the point at which a respective leg 38A, 38B and 38C of the frame assembly merges with the base portion 32. Each projection 52 is arranged to be releasably received within a correspondingly shaped opening (to be described hereinafter) in any of the disks 22A-22C to releasably secure or couple the frame assembly to the disks.

The frame assembly can be formed of any suitable lightweight, strong and inexpensive material, e.g., plastic. The frame assembly can be formed as an integral unit, such as by molding it, or it can be assembled of several components that are fixedly or releasably secured together.

Figure 6:
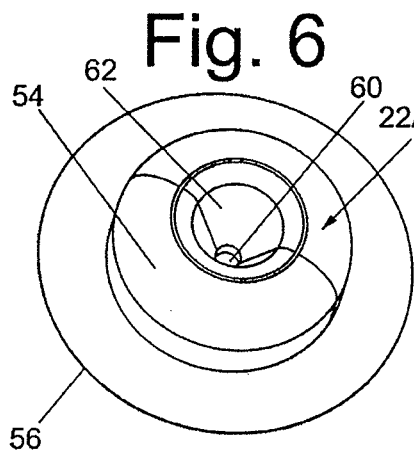
FIG. 6 is an enlarged isometric view of any of the releasably securable attachment members shown in FIGS. 1, 3 and 4 showing details of the top portion thereof.
Figure 7:
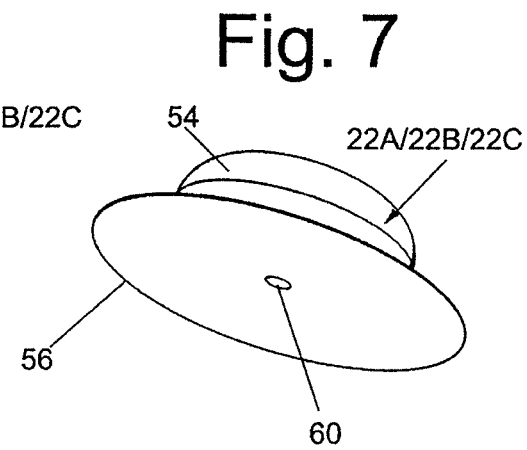
FIG. 7 is an enlarged isometric view of any of the releasably securable attachment members shown in FIGS. 1, 3 and 4 showing details of the undersurface thereof.

Turning now to FIGS. 6 and 7, the details of the adhesive disks 22A-22C will now be described. Each disk basically comprises a circularly shaped disk-like upper portion 54 having a circularly shaped flanged bottom 56. The undersurface 58 of the bottom 56 is in the form of a releasably securable adhesive. A releasable liner sheet (not shown) may be disposed over the adhesive on the undersurface 58 to protect the adhesive until the disk is ready for use. A central opening 60 extends through each of the disks from the undersurface of the disk (see FIG. 7) to its top surface. The top portion of the central opening 60 is flared at 62 as best seen in FIG. 6. The inside diameter of the opening 60 is just slightly larger than the outside diameter of the projections 52 of the frame assembly.

If desired, the base of the frame assembly 24 may include an adhesive undersurface (with or without a protective removable liner sheet) for releasably securing the frame assembly to the skin of the patient, in lieu of the use of the plural adhesive disks 22A-22C.

Figure 5:
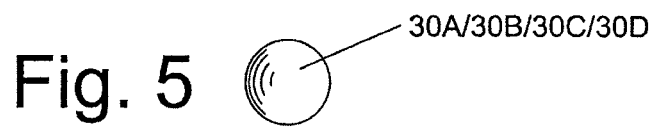
FIG. 5 is an enlarged isometric view of one exemplary visualizable reference imaging component, e.g., a ball, forming a portion of the frame assembly.

Turning now to FIG. 5, the details of the visualizable reference elements 30A-30D will now be described. Thus, each of those elements basically comprises a ball or sphere constructed of a material, e.g., titanium, brass, barium, stainless steel, etc., that can be readily imaged using conventional imaging modalities, e.g., X-ray, CT, MR, PET, etc. The reference elements 30A-30D are fixedly secured within respective correspondingly shaped recesses in the base portion 32 of the frame assembly.

The use of the marker device 20 will now be described. To that end, the disks 22A-22C are coupled to the frame assembly 24 by extending the frame assembly's projections 52 through the openings 60 in respective ones of the disks. If the disks had been equipped with liner sheets to protect the adhesive, those liner sheets will be removed prior to the coupling of the disks to the frame assembly, thereby exposing the adhesive undersurface of each of the disks. The frame assembly with the coupled disks can now be releasably secured to the skin of the patient at the desired location for the device 20, by merely pressing down on the disks to cause their adhesive undersurface to engage the patient's skin. If desired, the skin of the patient at the site of the device can be tattooed via the apertures 40A-40C.

If not already mounted on the frame assembly, the sensor assembly 26 can then be mounted thereon. To that end, the releasably mounting of the sensor assembly into the socket 34 of the frame assembly 24 is accomplished by orienting the sensor's housing 26A so that it is generally perpendicular to base portion 32 with its semicircular recess 46 pointed towards and aligned with the pin 44 extending across the end of the socket. The sensor's housing can then be mounted on the pin (i.e., the pin received within the recess) and once that has been accomplished, the sensor's housing can be rotated downward about the pin, whereupon the proximal end portion of the sensor's housing snap-fits between the projecting arms 36. This action releasably locks the sensor assembly 26 in the socket. The guide members 50 serve to guide the sensor assembly into this releasably locked position during the pivoting of the sensor's housing about the pin. In particular, when the sensor housing is rotated to lock it in place, the sloped surface of each guide member engages the outside surface of a respective one of the projecting arms 42 and rides over it until the sensor's housing is snap-fit or locked in the socket and is thus resistant from accidental disconnection.

As will be appreciated by those skilled in the art, once the marker device 20 of the subject invention is in place on the patient's skin it can be imaged by any suitable imaging modality, with the non-coplanar reference points being recorded. The EM sensor can be used to register the image to another image, as is conventional.

If and when it is desired to remove the sensor assembly 26 from the socket 24 all that is required is to rotate its proximal end upward, i.e., in the clockwise direction, so that its housing 26A passes between the projecting arms 36 of the socket. Once the sensor's housing is free of those arms, e.g., passes between the tabs 48, it can be removed from frame assembly for reuse. The frame assembly and the associated markers can be discarded when their use is no longer necessary.

Since the EM sensor 26 is a relatively expensive component designed to be reused, for some applications it may be desirable to isolate it from the ambient surroundings when it is being used in the device 20 in order to prevent it from being contaminated. To that end, a thin cover (not shown) shaped somewhat like a condom can be placed over the housing 26A of the sensor assembly 26 before mounting it in the socket of the frame assembly 24.

Figure 13:
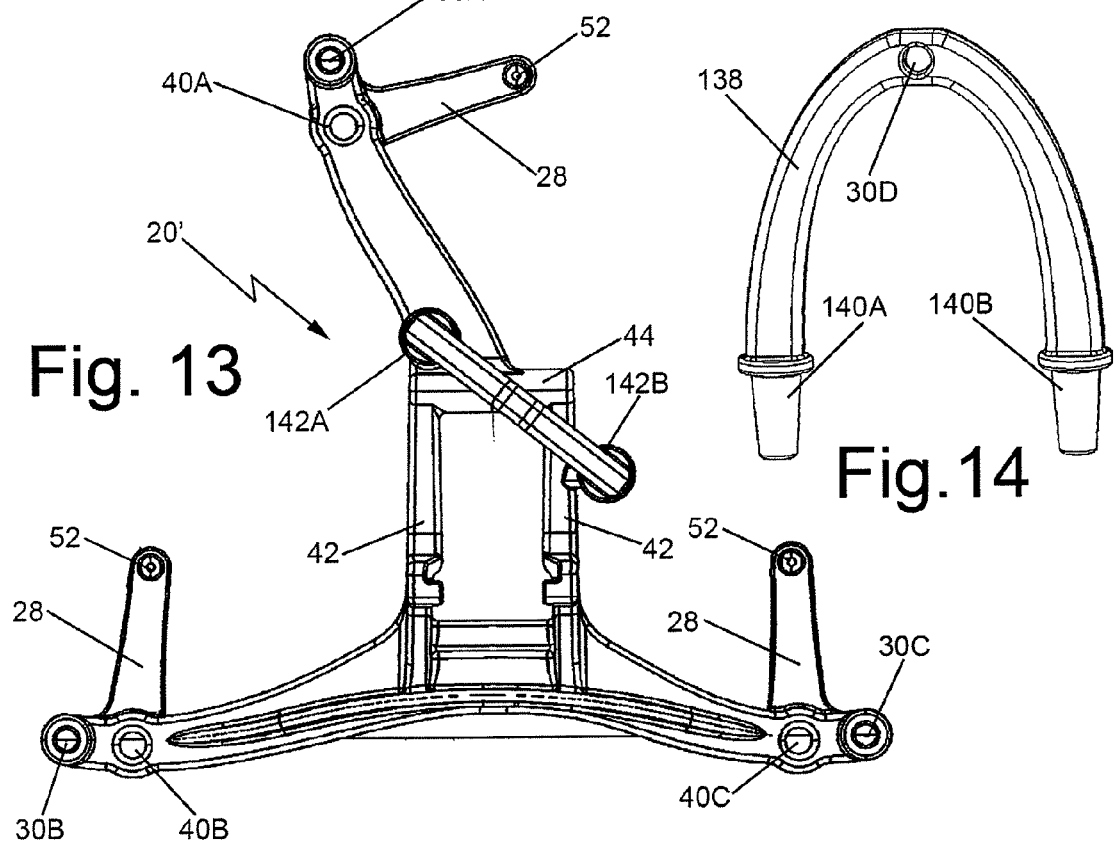
FIG. 13 is a top plan view of the alternative embodiment of the frame assembly shown in FIG. 12.
Figure 14:
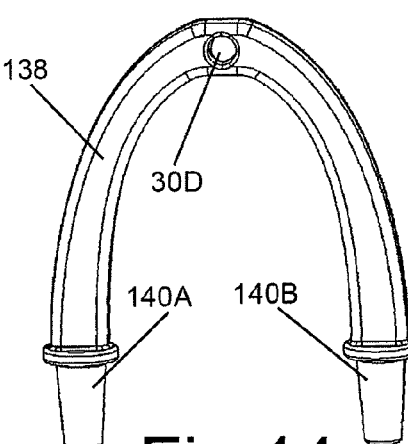
FIG. 14 is a front elevation view of one portion, i.e., an arch, of the alternative embodiment of the frame assembly shown in FIGS. 12 and 14.

It should be pointed out at this juncture that the exemplary embodiment of the marker device 20 shown and described heretofore is exemplary of various constructions and arrangements which can be utilized within the scope of this invention. Thus, various changes can be made to any of the components making up the marker device. For example, the frame assembly can be constructed wherein the frame's base portion (which can be constructed like component 32 described heretofore or some other construction) still is of a tripod-like, stable configuration established by plural skin-contact regions (e.g., the regions established by the adhesive disks 22A-22C), but does not include the three upstanding legs 38A-38C merging at a point at which one of the visualizable points (30D) is located. Thus, such alternative frame assembly embodiments may utilize any type structure, e.g., an arch, upstanding from the base portion and on the top of which a visualizable point (e.g., ball 30D) is located. This alternative embodiment is shown in FIGS. 12-14 and designated by the reference number 20'.

The embodiment 20' is identical to embodiment 20 except for an arch structure 138 (to be described shortly) being substituted for the three upstanding legs 38A-38C of embodiment 20. In the interest of brevity the common components between the embodiments 20 and 20' will be given the same reference numbers and the details of their construction and operation will not be reiterated.

Figure 12:
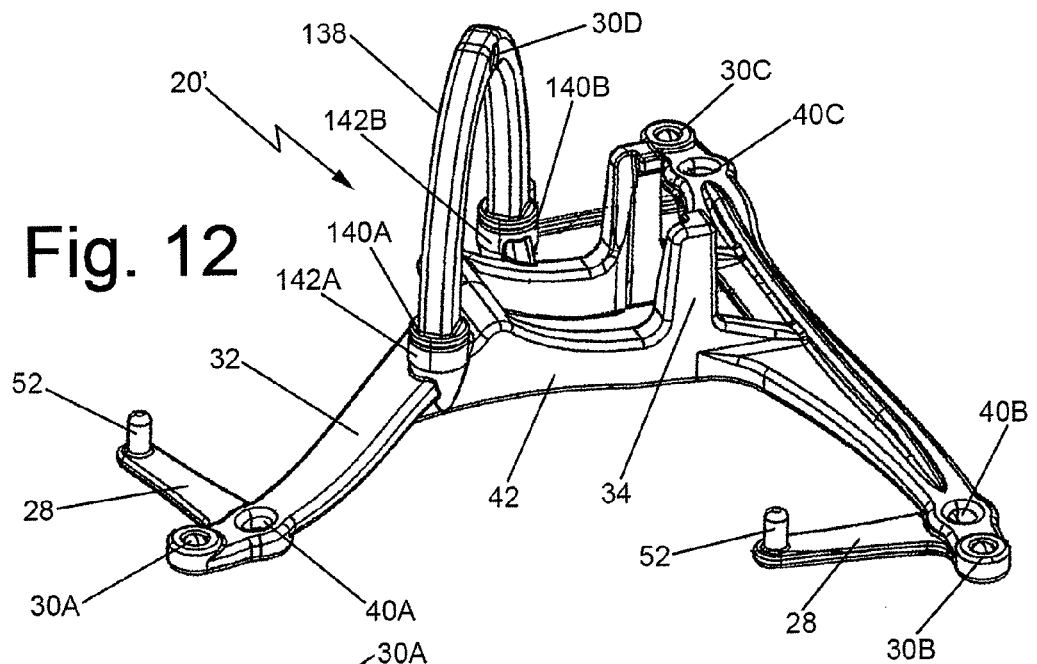
FIG. 12 is an isometric view of an alternative embodiment of a frame assembly of an active marker device constructed in accordance with this invention.

Thus, as can be seen in FIG. 12 the frame assembly includes an arch member 138 supporting the ball 30D on a front surface at the apex of the arch. The legs of the arch terminate in respective plugs 140A and 140B (FIG. 14) each of which tapers slightly. The plugs 140A and 140B are arranged to be received in respective sockets 142A and 142B of the base member 32.

Without further elaboration the foregoing will so fully illustrate our invention that others may, by applying current or future knowledge, adopt the same for use under various conditions of service.

We claim:

1. A marker device for use in an image-guided procedure on a patient, said marker device comprising an electromagnetic (EM) sensor, a frame, a plurality of visualizable elements, a plurality of projections, a plurality of openings, and a plurality of adhesive members, said visualizable elements being laterally spaced from said projections and not forming a portion of said projections, said electromagnetic (EM) sensor having a housing, each of said adhesive members having an adhesive surface, said frame comprising a single base portion, plural legs supported by said single base portion, and a socket mounted on said base portion for releasable receipt of said electromagnetic (EM) sensor housing, said legs projecting upward from said base portion and merging at a first location, each of said visualizable elements being formed of material that can be readily imaged by an imaging modality to establish imaging reference points, each of said visualizable elements being separate members from said frame, but being located on said frame adjacent respective legs of said frame with one of said visualizable elements being located at said first location and with the others of said visualizable elements located therebelow, with all of said visualizable elements defining a space therebetween, said socket being located within said space, each of said plural adhesive members being releasably coupled to said frame by the releasable receipt of a respective one of said projections within a respective one of said openings at locations adjacent said legs, said plurality of adhesive members also being configured to be releasably secured to the skin of the patient by said adhesive surfaces thereof to releasably secure said frame to the skin of the patient in a stable position and orientation without penetrating the skin of the patient.

2. The marker device of claim 1 wherein each of said adhesive members comprises a disk.

3. The marker device of claim 2 wherein each of said projections has an outside diameter and each of said openings has an inside diameter, with said inside diameter of said openings being just slightly larger than said outside diameter of said projections.

4. The marker device of claim 1 wherein each of said adhesive members includes a respective one of said openings.

5. The marker device of claim 1 wherein said electromagnetic (EM) sensor housing is arranged to be snap-fit into said socket.

6. The marker device of claim 5 wherein said electromagnetic (EM) sensor housing is arranged to be pivotably coupled to said frame assembly to snap-fit into said socket.

7. The marker device of claim 6 wherein one of said socket and said electromagnetic (EM) sensor housing includes a pin member and the other of said socket and said electromagnetic (EM) sensor housing includes a correspondingly shaped recess, said pin member being arranged to be received in said recess to enable said electromagnetic (EM) sensor housing to be pivoted with respect to said socket to snap-fit said electromagnetic (EM) sensor housing into said socket.

8. The marker device of claim 7 wherein said electromagnetic (EM) sensor housing includes said recess and said socket includes said pin.

9. The marker device of claim 8 wherein said socket is located in said base portion.

10. The marker device of claim 1 wherein said frame assembly comprises plural apertures therein, each of said apertures being arranged to provide an access point to enable the marking of the skin of the patient with indicia through said aperture.

11. The marker device of claim 10 wherein said plural apertures are asymmetrically disposed with respect to each other, with each of said plural apertures being located in said base portion adjacent a respective one of said legs.

\* \* \* \* \*